United States Patent [19]

Kim et al.

[11] Patent Number: 5,356,438
[45] Date of Patent: Oct. 18, 1994

[54] HAIR COLOR RINSE COMPOSITION CONTAINING HALOGINATED FLUORESCEIN DYES

[75] Inventors: Chang K. Kim, Seoul; Jin K. Cha, Suwon; Eung S. Kang, Seoul, all of Rep. of Korea

[73] Assignee: Pacific Corporation, Seoul, Rep. of Korea

[21] Appl. No.: 1,645

[22] Filed: Jan. 7, 1993

[30] Foreign Application Priority Data

Oct. 16, 1992 [KR] Rep. of Korea ............... 92-19056

[51] Int. Cl.$^5$ ............................................. A61K 7/13
[52] U.S. Cl. ............................................. 8/405; 8/435; 8/581; 8/648; 424/70
[58] Field of Search ............... 8/405, 429, 435, 581, 8/648; 424/70; 252/DIG. 13

[56] References Cited

U.S. PATENT DOCUMENTS

| | | | |
|---|---|---|---|
| 3,873,687 | 3/1975 | Demko | 424/64 |
| 3,930,792 | 1/1976 | Alperin et al. | 8/10.1 |
| 4,781,724 | 11/1988 | Wajaroff et al. | 8/432 |
| 4,849,127 | 7/1989 | Maxon | 252/DIG. 13 |
| 4,873,079 | 10/1989 | Hahn et al. | 8/405 |
| 5,094,662 | 3/1992 | Schultz et al. | 8/405 |

FOREIGN PATENT DOCUMENTS 1033302 6/1978 Canada .

OTHER PUBLICATIONS

Burgess Cosmetics and Perfumery vol. 88, Oct. 1973, pp. 49-56 "Effect of formulation upon deposition from cosmetic and toiletry products".

Primary Examiner—Paul Lieberman
Assistant Examiner—Caroline L. Dusheck
Attorney, Agent, or Firm—Nixon & Vanderhye

[57] ABSTRACT

A hair color rinse composition that simultaneously dyes and conditions hair which comprises a tinctorial amount of one or more acidic dyes, from about 0.01 to 0.5 parts by weight based on the total weight of the composition of one or more halogenated fluorescein dyes and from about 1.0 to 20.0 parts by weight based on the total weight of the composition of a disodium dimethicone copolyol sulfosuccinate is disclosed.

4 Claims, No Drawings

HAIR COLOR RINSE COMPOSITION CONTAINING HALOGINATED FLUORESCEIN DYES

FIELD OF THE INVENTION

The present invention relates to compositions for dyeing and conditioning hair, and more particularly, it relates to hair color rinse compositions which are designed to impart even color to human hair in a short time as well as to impart an improved sheen and texture, when applied to the hair.

BACKGROUND OF THE INVENTION

Hair dye products can be classified into four main groups: (a) color rinses; (b) metallic dyes; (c) semipermanent preparations; and (d) permanent types based upon oxidation dyestuffs. The hair color rinse products impart color and at the same time manageability by applying them to the hair after shampooing and rinsing. They are advantageous in their ease application.

However, because most hair color rinse compositions contain acid dyes which can impart even color and do not damage hair, they are disadvantageous in that the color, after application to the hair is washed out with relative ease, indicating that the deposition of dye onto the hair is insufficient. Therefore, in order to impart color to hair with considerable fastness, several applications of color rinse compositions to the hair or long period contact with the hair is required.

Incorporating basic dyes into hair color rinse compositions has been proposed to improve dyeing effectiveness. But, the use of basic dyes has the disadvantages of instability and skin staining. Furthermore, the basic dye compositions tend to give uneven dyeing, the dye uptake being greater along certain portions of the hair shaft, especially the portions of damagend hair, than others.

Many attempts have been made to improve deposition of the dye onto the hair from hair color rinse compositions. For example, the take-up of the dye from the composition by the hair is improved by adjusting the composition to slightly acidic conditions with tartaric or sulphamic acid. Another method consists of pretreating the hair with a cationic synthetic detergent, $C_{11}H_{23}COO.CH_2.C.(CH_3)_2 NH_3^+ -OOC.CH_3$. Further, an attempt to improve take-up of dye by the hair includes the use of organic solvents such as 2-phenoxyethanol, benzyl alcohols and other related alcohols which enable a greater concentration of dystuff to be dissolved or dispersed in the formula and improve the rate of uptake and fixation of the dye on the hair. However, these solvents irritate the skin and many countries restrict their use in the cosmetics.

Accordingly, there has been a need for hair color rinse compositions which are designed to impart even, natural color to human hair in a shorter time and to impart an improved sheen and texture, when applied to the hair and which does not irritate the skin.

The present inventors have made extensive studies to provide hair color rinse compositions which meet the above-mentioned needs, and as a result thereof, found that this can be accomplished by including both of a halogenated fluorescein dye and a disodium dimethicone copolyol sulfosuccinate in hair color rinse compositions.

SUMMARY OF THE INVENTION

Thus, one of the objects of the present invention is to provide a hair color rinse composition which imparts an even, natural color to human hair in a shorter time and does not irritate the skin.

Another object of the present invention is to provide a hair color rinse composition which contains a halogenated fluorescein dye and disodium dimethicone copolyol sulfosuccinate, thereby imparting an even natural color to human hair in a shorter time without irritating the skin.

Still another object of the invention is to provide a hair color rinse composition which contains a tinctorial amount of one or more acidic dyes, from about 0.01 to 0.5 parts by weight based on the total weight of the composition of one or more halogenated fluorescein dyes and from about 1.0 to 20.0 parts by weight based on the total weight of the composition of disodium dimethicone copolyol sulfosuccinate.

A further object of the invention is to provide a method for simultaneously dyeing and conditioning hair by applying the above composition to hair and allowing this composition to remain in contact with the hair for a sufficient time to impart color to the hair and to condition leaving the hair more manageable and with even, natural color.

DETAILED DESCRIPTION OF THE INVENTION

According to the present invention, halogenated fluorescein dyes are employed to enhance the uptake of the acid dyes from the hair color rinse composition by tile hair and may be represented by the following formula(I):

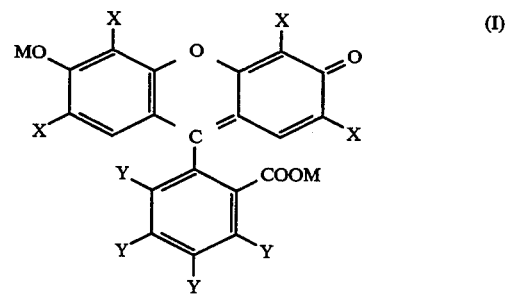

or formula (I'):

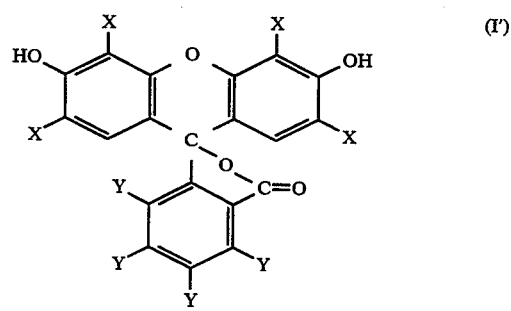

wherein,

X, which are the same or different from each other, is a hydrogen atom or a halogen atom selected from the group consisting of chlorine, bromine and iodine, provided at least two of the 4 X's are halogen atoms, Y, all of which should be the same as each other, is a hydrogen atom or a halogen atom selected from the group consisting of chlorine and bromine, and M, is a hydrogen atom or a metal selected from the group consisting of Na and K.

The halogenated fluorescein dyestuffs of the formula(I) or (I') may include, but not limited to, D&C Red No. 28[Phloxine B, Disodium salt of 2,4,5,7-tetrabromo-9-(3,4,5,6-tetrachloro-o-carboxyphenyl)-6-hydroxy-3-isoxanthone], CI No. 45440 (Rose bengal, Disodium salt of 9-(3,4,5,6-tetrachloro-o-carboxyphenyl-6-hydroxy-2,4,5,7-tetraiodo-3-isoxanthone], D&C Red No. 19 [Rhodamine, 3-Ethochloride of 9-o-carboxyphenyl-6-diethylamino-3-ethylamino-3-isoxanthene], D&C Red No. 27 [Tetrachlorotetrabromofluorescein, 2,4,5,7-Tetrabromo-12,13,14,15-tetrachloro-3,6-fluorandiol], D&C Red No. 21 [Tetrabromofluorescein, 2, 4, 5, 7-Tetrabromo-3,6-fluorandiol], D&C Red No. 22 [Eosine YS, Disodium salt of 2,4,5,7-Tetrabromo-9-o-carboxyphenyl-6-hydroxy-3-isoxanthone], D&C Red No. 23 [Eosine YSK, Dipotassium salt of 2,4,5,7-tetrabromo-9-o-carboxyphenyl-6-hydroxy-3-isoxanthone], C.I. 45410 Acid Red 92 [Phloxine BK, Dipotassium salt of 2,4,5,7-tetrabromo-9-( 3,4,5,6-tetrachloro-o-carboxyphenyl)-6-hydroxy-2,4,5,7-tetraiodo-3-isoxanthone], D&C Orange No. 5 [Dibromofluorescein, 4,5- Dibromo-3,6-fluorandiol], D&C Orange No. 10 [Diiodofluoresceine, 4,5-Diiodo-3,6-Fluorandiol] or D&C Orange No. 11 [Erythrosine Yellow NA, Disodium salt of 9-o-carboxyphenyl-6-hydroxy-4,5-diiodo-3-isoxanthone]. The dyes may be employed in alone or mixtures thereof. The halogenated fluorescein dyestuffs exhibit red or blue color when deposited onto the hair, and the more halogenated the dyes are, the deeper the blue color is. The fastness of the deposited color is strongest when both of resorcine and phthalic rings are halogenated.

The halogenated fluorescein dyestuffs used in the present invention are demonstrated to be safe for use on the human body and have been widely used in lipstick formulations.

Since the halogenated fluorescein dyes themselves serve as a colorant as well as to improve the uptake of acidic dyes by the hair from the hair color rinse composition, the composition according to the present invention provides a sufficient deposition of dyes onto the hair even when the composition is in control with the hair for only a short time.

The particular amount of halogenated fluorescein dye that will be contained in the hair color rinse composition of the invention will vary depending on the shade desired and the relative quantities of other ingredients. In general, however, the halogenated fluorescein constitutes between about 0.001 and 1 parts by weight, and preferably from 0.01 to 0.5 parts by weight based on the total weight of the composition.

Improvement of dye uptake by an inclusion of halogenated fluorescein can be further enhanced by incorporating the composition disodium dimethicone copolyol sulfosucinate having a molecular weight of from 10,000 to 30,000.

The disodium dimethicone copolyol sulfosuccinate imparts conditioning ability in addition to increasing the uptake of the dyes by the hair from the composition. The disodium dimethicone copolyol sulfosuccinate useful in the invention may be any one selected from those commonly used in hair-care cosmetic compositions. They are commercially available, and the present invention employs Mackanate DC30 manufactured by Mcintyre Co., Ltd.

The particular quantity of disodium dimethicone copolyol sulfosuccinate that will be contained in the hair color rinse composition of this invention will vary depending on the relative quantities of the other ingredients and the particular results that are sought. In general, however, this compound is contained in an amount from 0.1 to 20.0 parts by weight based on the total weight of the composition.

As mentioned above, in accordance with the present invention, the combined inclusion of both halogenated fluorescein dyes and disodium dimethicone copolyol sulfosuccinate make it possible for the hair color rinse composition of the invention to impart even, natural color to the hair in a shorter time, and cause no irritation to the skin nor damage to the hair.

An essential component of the compositions of the invention is the acid dye, which is exemplified by FD&C Red No. 2 (Amaranth), FD&C Red No. 3 (Erythrosine), C.I. 16255 Acid Red 18 (New coccin), C.I. 45100 Acid Red 52 (Acid Red), FD&C Yellow No. 5 (Tartrazine), FD&C Yellow No. 6 (Sunset yellow FCF), FD&C Green No. 3 (Fast green FCF), FD&C Blue No. 1 (Brilliant blue FCF), FD&C Blue No. 2 (Indigo carmine), D&C Red No. 33 (Fast acid magenta), D&C Green No. 5 (Alizanine cyanine green F), D&C Green No. 4 (Light green SF yellowish), D&C Blue No. 4 (Alfazurine FG), D&C orange No. 4 (Orange II), FD&C Red No. 4 (Ponceau SX), Ext. D&C Violet No. 2 (Alizurol purple), D&C Black No. 1 (Naphtol blue black) and the like.

The particular type of dye which will be contained in the composition of this invention will vary depending on the shade desired and its selection is routine and obvious for those skilled in the art. The amount of the acid dye incorporated into the composition will vary depending upon the shade desired and the relative quantities of the other ingredients. In general, however, the acid dye constitutes between about 0.01 and 2.0 parts by weight based on the total weight of the composition.

The hair color rinse compositions according to the invention may comprise, in addition to the above halogenated fluorescein dye(s), disodium dimethicone copolyol sulfosuccinate and acid dyes, other ingredients which are commonly employed in the hair color rinse compositions, such as surface active agents, thickening agents, oils, fatty alcohols, pH adjusting agents, water and other conventional ingredients.

The surface active agents which can be employed in the present invention may include, but not limited to, anionic surfactants such as sodium lauryl sulfate, sodium polyoxyethylene lauryl ether sulfate, sodium lauryl sulfate, diethanolamindo lauryl sulfate, diethanolamido polyoxyethylene lauryl ether sulfate, triethanolamido lauryl sulfate, triethanolamido polyoxyethylene lauryl ether sulfate, disodium cocamido MIPA sulfosuccinate, potassium cocohydrolyzed animal protein, TEA cocohydrolyzed animal protein, sodium cocoyl glutamate, TEA cocoyl glutamate, sodium lauroyl glutamate, TEA lauroyl glutamate, sodium lauroyl sarcosinate, sodium cocoyl sarcosinate and sodium lauroyl tartrate, amphoteric surfactants such as cocoamphocarboxy glycinate, disodium cocoamphopropionate, cocoamphopropionate, lauroamphocarboxypropionate, o lauroamphoglycinate, lauroamphopropionate, cocamidopropyl betaine, luramido propyl betaine, coco-betaine, lauryl betaine, and cationic surfactants such as alkyldimethylbenzylammonium chloride, alkyl trimethylammonium chloride, dialkyldimethylammonium chloride. These surface active agents may be employed in alone or mixtures thereof. The quantity of the surface active agents employed can vary over a wide range, depending on the dye and the particular surface active agent employed. Illustratively, the agent can vary from about 0.1 to about 10.0 parts by weight of the composition.

A thickening agent can also be incorporated in the hair color rinse compositions of the invention, which may be one of those commonly used in hair rinse compositions, such as hydroxypropylcellulose, hydroxypropyl methylcellulose, hydroxyethyl methylcellulose, polyquaternium-7, polyquaternium-10, carboxymethyl guar, carboxymethylhydroxyl quar, PEG-120 methylglucosyl dioleate and the like. The quantity of this thickening agent, which is not critical in the invention, can vary over a wide range and may be determined without difficulty by a person oridinarily skilled in the art.

The adopted names used to exemplify the surface active agents and thickening agents herein are from the "CTFA Cosmetic Ingredient Dictionary" 3rd ed., published by The Cosmetic, Toiletry and Fragrance Association, Inc., 1110 Vermont Avenue, N.W., Washington D.C. 20005. These terms are well known to those skilled in the art.

The oils, which may be employed in the invention, can be exemplified, but not limited to, wheat germ oil, jojoba oil, sesame oil, safflower oil, soybean oil, corn oil, mineral oil, carrot oil, peach kernel oil and the like. The quantity of this oil, which is not critical to the invention, can vary over a wide range and may be determined without difficulty by a person ordinarily skilled in the art.

The fatty alcohols, which can be incorporated in the compositions of the invention, may include, but not limited to, cetyl alcohol, stearyl alcohol, cetearyl alcohol, benzyl alcohol, capyrlic alcohol, coconut alcohol, decyl alcohol, lauryl alcohol, myristyl alcohol, oleyl alcohol, tallow alcohol, palm kernel alcohol, tridecyl alcohol and the like.

The pH of the present hair color rinse compositions can vary widely, however, it varies preferably from about 3.0 to 5.0. The pH of the compositions may be adjusted with any inorganic or organic acid or acid salt which is compatible with the composition. Illustrative acids include sulfuric, lactic, formic, acetic, tartaric, citric, phosphoric, boric or glycolic acid.

The hair color rinse compositions can be applied to prematurely gray hair, gray hair, white hair, silver or blond hair. The composition also can be applied to brown or black hair. The composition can be applied to hair by conventional techniques used in the art. Illustratively, when applied to semi-long hair, about 5 to 20 ml of the composition can be applied to the wet hair after shampooing and is allowed to remain in contact with the hair for sufficient time to impart color to the hair, for example for about 30 sec to 3 min. The desired deposition of dye can be attained by repeating the above procedure about 5 to 6 times. The time of contact of the hair color rinse composition with the hair may be extended in order to attain sufficient deposition of dye on the hair with two or three applications of the composition. And, when applied to brown or black hair, considerable color may be imparted to the hair by extending the time of contact or increasing the frequency of application.

The following Formulation Examples are given to further illustrate the present invention. It is to be understood, however, that they are not intended to be limitative but merely exemplary of the present invention.

FORMULATION EXAMPLES 1 to 5

The formulations given in Table 1 below were prepared by the following procedure:

Hydroxyethyl cellulose was added to and dissolved in water by heating under stirring. Methyl paraoxybenzoate and nonoxinol-9 were dissolved in ethanol and the resulting solution was mixed with the solution obtained above. To the resulting mixture were added dyes and the mixture was stirred until a uniform solution was obtained. The pH of the solution was adjusted to 3.0–5.0 with phosphoric acid and the perfume was added.

TABLE 1

| Ingredients | Formulation Ex. 1 (Comparative) | Formulation Ex. 2 (Comparative) | Formulation Ex. 3 (Inventive) | Formulation Ex. 4 (Comparative) | (parts by weight) Formulation Ex. 5 (Comparative) |
|---|---|---|---|---|---|
| Hydroxyethyl cellulose | 0.5 | 0.5 | 0.5 | 0.5 | 0.5 |
| Benzyl alcohol | 5.0 | — | — | — | — |
| Ethanol | — | 5.0 | 5.0 | 5.0 | 5.0 |
| Nonoxinol-9 | 1.0 | 1.0 | 1.0 | 1.0 | 1.0 |
| Methyl paraoxybenzoate | 0.2 | 0.2 | 0.2 | 0.2 | 0.2 |
| Acidic dye 1 (EXT. D&C Violet No. 2) | 0.02 | 0.02 | 0.02 | 0.02 | 0.02 |
| Acidic dye 2 (D&C Black No. 1) | 0.01 | 0.01 | 0.01 | 0.01 | 0.02 |
| Acidic dye 3 (D&C Orange No. 4) | 0.01 | 0.01 | 0.01 | 0.01 | 0.02 |
| Disodium dimethicone copolyol sulfosuccinate* | — | 10.0 | 10.0 | — | — |
| Dye 1 (D&C Red No. 22) | — | — | 0.02 | 0.02 | — |
| Perfume | q.s. | q.s. | q.s. | q.s. | q.s. |
| Phosphoric acid | q.s. | q.s. | q.s. | q.s. | q.s. |
| Distilled water | q.s. | q.s. | q.s. | q.s. | q.s. |

Note
1: Dye 1 is halogenated fluorescein dyestuff.
2: *= Mackanate DC 30 manufactured by McIntyre Co., Ltd.

In order to examine the deposition of dyes, the formulations obtained above were applied to a defatted gray wool cloth and, after 3 minutes, the cloth was thoroughly rinsed with a running water. The results of color comparison with naked eyes showed that formulation 1 colored the cloth a brown shade which is as deep as that of formulation 2, while formulation 3 colored the cloth the deepest shade. Formulation 4 which contains 0.02 parts by weight of D&C Red No. 22 showed a far better dye deposition than formula 5 which contains halogenated fluorescein dyes.

In order to examine the conditioning properties, a tress (2g) of dark brown hair 20 cm long was shampooed and each of formulations 1 to 5 was applied to the wet tress. After 3 min, the tress was rinsed with a running water and dried with a hair drier. Then, the texture, sheen and manageability of the hair and, after vigorously combing the hair, fly-off of the hair were examined. The results show that the tresses treated with formulations 2 and 3 which contain disodium dimethicone copolyol sulfosuccinate showed an improved texture and sheen, and became more manageable and prevented fly-off.

The deposition of dyes and conditioning properties of formulations 6 to 9 were examined as described in Formulation Examples 1 to 5.

It was found that formulations 7 and 9 which contain D&C Red. No. 28 as a halogenated fluorescein dye colored the cloth a considerably deep brown shade and formulation 9 which contains D&C Red No. 22 in combination with disodium dimethicone copolyol sulfosuccinate colored the cloth a deepest brown shade. Further, formulations 8 and 9 which contain disodium dimethicone copolyol sulfosuccinate show excellent conditioning properties.

FORMULATION EXAMPLES 10 to 15

By following the procedure in Formulation Examples 1 to 5, formulations 10 to 15 shown in Table 3 below were prepared.

TABLE 3

| Ingredients | Formulation Ex. 10 (Comp.) | Formulation Ex. 11 (Inventive) | Formulation Ex. 12 (Comp.) | Formulation Ex. 13 (Comp.) | Formulation Ex. 14 (Comp.) | (parts by weight) Formulation Ex. 15 (Inventive) |
|---|---|---|---|---|---|---|
| Hydroxyethyl cellulose | 0.5 | 0.5 | 0.5 | 0.5 | 0.5 | 0.5 |
| Ethanol | 5.0 | 5.0 | 5.0 | 5.0 | 5.0 | 5.0 |
| Nonoxinol-12 | 1.0 | 1.0 | 1.0 | 1.0 | 1.0 | 1.0 |
| Methyl paraoxybenzoate | 0.2 | 0.2 | 0.2 | 0.2 | 0.2 | 0.2 |
| Acidic dye 1 (EXT. D&C Violet No. 2) | 0.01 | 0.01 | 0.01 | 0.01 | 0.01 | 0.01 |
| Acidic dye 2 (D&C Black No. 1) | 0.03 | 0.02 | 0.03 | 0.02 | 0.01 | 0.01 |
| Acidie dye 3 (D&C Orange No. 4) | 0.02 | 0.01 | 0.02 | 0.01 | 0.01 | 0.01 |
| Disodium dimethicone copolyol sulfosuccinate* | — | 10.0 | 10.0 | — | — | 10.0 |
| Dye 1 (D&C Red No. 27) | — | 0.01 | — | 0.01 | 0.02 | 0.02 |
| Dye 2 (D&C Red No. 21) | — | 0.01 | — | 0.01 | 0.01 | 0.01 |
| Perfume | q.s. | q.s. | q.s. | q.s. | q.s. | q.s. |
| Citric acid | q.s. | q.s. | q.s. | q.s. | q.s. | q.s. |
| Distilled water | q.s. | q.s. | q.s. | q.s. | q.s. | q.s. |

Note
1: Dye 1 and 2 are halogenated fluorescein dyestuffs.
2: *= Mackanate DC 30 manufactured by McIntyre Co., Ltd.

FORMULATION EXAMPLES 6 to 9

By following the procedure in Formulation Examples 1 to 5, formulations 6 to 9 shown in Table 2 below were prepared.

The deposition of dyes and conditioning properties of formulations 10 to 15 were examined as described in Formulation Examples 1 to 5.

When compared with formulations 10 to 13, formulations 11 and 13 which contain hydrogenated fluorescein dyes(Dyes 1 and 2) colored the cloth a deeper shade

TABLE 2

| Ingredients | Formulation Ex. 6 (Comparative) | Formulation Ex. 7 (Comparative) | Formulation Ex. 8 (Comparative) | (parts by weight) Formulation Ex. 9 (Inventive) |
|---|---|---|---|---|
| Hydroxyethyl cellulose | 0.5 | 0.5 | 0.5 | 0.5 |
| Ethanol | 5.0 | 5.0 | 5.0 | 5.0 |
| Nonoxinol-9 | 1.0 | 1.0 | 1.0 | 1.0 |
| Methyl paraoxybenzoate | 0.2 | 0.2 | 0.2 | 0.2 |
| Acidic dye 1 (EXT. D&C Violet No. 2) | 0.02 | 0.02 | 0.02 | 0.02 |
| Acidic dye 2 (D&C Black No. 1) | 0.02 | 0.01 | 0.02 | 0.01 |
| Acidic dye 3 (D&C Orange No. 4) | 0.02 | 0.01 | 0.02 | 0.01 |
| Disodium dimethicone copolyol sulfosuccinate* | — | — | 10.0 | 10.0 |
| Dye 1 (D&C Red No. 22) | — | 0.02 | — | 0.02 |
| Perfume | q.s. | q.s. | q.s. | q.s. |
| Phosphoric acid | q.s. | q.s. | q.s. | q.s. |
| Distilled water | q.s. | q.s. | q.s. | q.s. |

Note
1: Dye 1 is halogenated fluorescein dyestuff.
2: *= Mackanate DC 30 manufactured by McIntyre Co., Ltd.

than those colored by formulations 10 and 12 which contain no hydrogenated fluorescein dye. And, formulation 11 which contained the hydrogenated fluorescein dyes together with disodium dimethicone copolyol sulfosuccinate colored the cloth the deepest shade.

Further, formulation 15 which contains 0.03 parts by weight of halogenated fluorescein dyes (0.02 parts by weight of Dye 1 plus 0.01 parts by weight of Dye 2) colored cloth a deeper shade than the formulation 11 which contains 0.02 parts by weight of halogenated fluorescein dyes(0.01 parts by weight of Dye 1 plus 0.01 parts by weight of Dye 2).

Formulations 11, 12 and 15 which contain disodium dimethicone copolyol sulfosuccinate show excellent conditioning properties.

As described above, the hair color rinse compositions according to the present invention impart an even, natural color to human hair in a relatively short time when applied to such hair yet they do not irritate the skin due to the absence of benzyl alcohol, and they contain one or more halogenated fluorescein dyes and a disodium dimethicone copolyol sulfosuccinate.

Although the invention has been described with reference to the preferred embodiments thereof, it will be understood that many changes and modifications may be made without departing from the spirit of the present invention which is limited only by the scope of the claims appended hereto.

What is claimed is:

1. A hair color rinse composition consisting essentially of:

(a) from about 0.01 to 2.0 parts by weight, based on the total weight of the composition, of at least one acid dye selected from the group consisting of FD&C Red 2, FD&C Red 3, C.I. 16255 Acid Red 18, C.I. 45100 Acid Red 52, FD&C Yellow 5, FD&C Yellow 6, FD&C Green 3, FD&C Blue 1, FD&C Blue 2, D&C Red 33, D&C Green 5, D&C Green 4, D&C Blue 4, D&C Orange 4, FD&C Red 4, Ext. D&C Violet 2 and D&C Black 1;

(b) from about 0.01 to 0.5 parts by weight, based on the total weight of the composition, of at least one halogenated fluorescein dye of the formula:

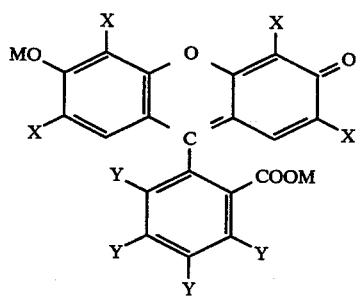

or

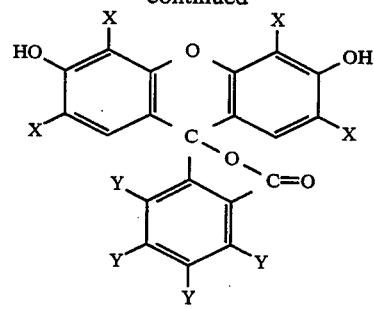

wherein,

X, which may be the same or different, is a hydrogen atom or a halogen atom selected from the group consisting of chlorine, bromine and iodine, provided that at least two of the 4 X's are halogen atoms, Y, all of which are the same, is a hydrogen atom or a halogen atom selected from the group consisting of chlorine and bromine, M is a hydrogen atom or a metal selected from the group consisting of Na and K; and (c) from about 1.0 to 20.0 parts by weight, based on the total weight of the composition, of disodium dimethicone copolyol sulfosucinate having molecular weight of from 10,000 to 30,000.

2. The composition according to claim 1 in which the halogenated fluorescein dyes are selected from the group consisting of D&C Red No. 28 of the chemical name Phloxine B, Disodium salt of 2,4,5,7-tetrabromo-9-(3,4,5,6-tetrachloro-o-carboxyphenyl)-6-hydroxy-3-isoxanthone], CI No. 45440 of the chemical name Rose bengal, Disodium salt of 9-(3,4,5,6-tetrachloro-o-carboxyphenyl-6-hydroxy-2,4,5,7-tetraiodo-3-isoxantIone], D&C Red No. 19 of the chemical name Rhodamine, 3-Ethochloride of 9-o-carboxyphenyl-6-diethylamino-3-ethylamino-3-isoxanthene], D&C Red No. 27 of the chemical name Tetrachlorotetrabromofluorescein, 2,4,5,7-Tetrachloro-12,13,14,15-tetrachloro-3,6-fluorandiol], D&C Red No. 21 of the chemical name Tetrabromofluorescein, 2,4,5,7-Tetrabromo-3,6fluorandiol. D&C Red No. 22 of the chemical name Eosine YS, Disodium salt of 2,4,5,7-Tetrabromo-9-o-carboxyphenyl-6-hydroxy-3-isoxanthone], D&C Red No. 23 of the chemical name Eosine YSK, Dipotassium salt of 2,4,5,7-tetrabromo-9-o-carboxyphenyl-6-hydroxy-3-isoxanthone], C.I. 45410 Acid Red 92 of the chemical name Phloxine BK, Dipotassium salt of 2,4,5,7-tetrabromo-9-(3,4,5,6-tetrachloro-o-carboxyphenyl)-6-hydroxy-2,4,5,7-tetrachloro-3-isoxanthone], D&C Orange No. 5 of the chemical name Dibromofluorescein, 4,5-Dibromo-3,6-fluorandiol. D&C Orange No. 10 of the chemical name Diiodofluoresceine, 4,5-Diiodo-3,6-Fluorandiol, and D&C Orange No. 11 of the chemical name Erythrosine Yellow NA, Disodium salt of 9-o-carboxyphenyl-6-hydroxy-4,5-diiodo-3-isoxanthone.

3. The composition according to claim 1 in which the pH of the composition is adjusted to 3.0 to 5.0.

4. A process for simultaneously dyeing and conditioning hair which comprises applying a hair color rinse to hair and allowing said composition to remain in contact with the hair for a time sufficient to impart color to the hair whereby the hair becomes more manageable and has a natural, even color, wherein said hair color rinse composition consists essentially of (a) from about 0.01 to 2.0 parts by weight, based on the total weight of the composition, of at least one acid dye selected from the group consisting of FD&C Red 2, FD&C Red 3, C.I. 16255 Acid Red 18, C.I 45100 Acid Red 52, FD&C Yellow 5, FD&C Yellow 6, FD&C Green 3, FD&C Blue 1, FD&C Blue 2, D&C Red 33, D&C Green 5, D&C Green 4, D&C Blue 4, D&C Orange 4, FD&C Red 4, Ext. D&C Biolet 2 and D&C Black 1;

(b) from about 0.01 to 0.5 parts by weight, based on the total weight of the composition, of at least one halogenated fluorescein dye of the formula:

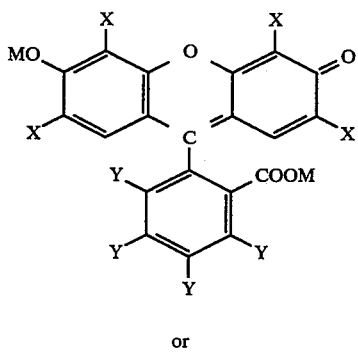

or

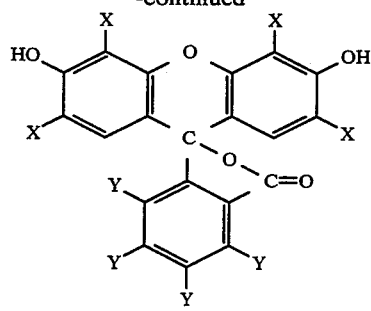

wherein,

X, which may be the same or different, is a hydrogen atom or a halogen atom selected from the group consisting of chlorine, bromine and iodine, provided that at least two of the 4 X's are halogen atoms, Y, all of which are the same, is a hydrogen atom or a halogen atom selected from the group consisting of chlorine and bromine, M is a hydrogen atom or a metal selected from the group consisting of Na and K; and (c) from about 1.0 to 20.0 parts by weight, based on the total weight of the composition, of disodium dimethicone copolyol sulfosuccinate having molecular weight of from 10,000 to 30,000.

* * * * *